United States Patent [19]

Akimoto et al.

[11] Patent Number: 5,128,250
[45] Date of Patent: * Jul. 7, 1992

[54] PROCESS FOR PRODUCTION OF HIGHLY UNSATURATED FATTY ACID HAVING ODD NUMBER OF CARBON ATOMS

[75] Inventors: Kengo Akimoto, Osaka; Yoshifumi Shinmen, Kyoto; Hideaki Yamada, Kyoto; Sakayu Shimizu, Kyoto, all of Japan

[73] Assignee: Suntory Limited, Osaka, Japan

[*] Notice: The portion of the term of this patent subsequent to Apr. 10, 2007 has been disclaimed.

[21] Appl. No.: 321,095

[22] Filed: Mar. 9, 1989

[30] Foreign Application Priority Data

Mar. 9, 1988 [JP] Japan ................................. 63-53641

[51] Int. Cl.$^5$ .......................... C12P 7/64; C12N 1/38; C12N 1/28; C12N 1/14
[52] U.S. Cl. .................................. 435/134; 435/911; 435/244; 435/249
[58] Field of Search ............... 435/134, 911, 135, 136, 435/132, 131, 244

[56] References Cited

U.S. PATENT DOCUMENTS 4,783,408  11/1988  Suzuki et al. ....................... 435/134
4,851,343   7/1989  Herbert et al. ..................... 435/134
4,916,066   4/1990  Akimoto et al. .................... 435/134

FOREIGN PATENT DOCUMENTS 0276982  8/1988  European Pat. Off. ............ 435/134
3263088 10/1988  Japan ................................. 435/134

OTHER PUBLICATIONS

Hoffmann, B., and Rehm, H. J. 1978. "Degradation of Long-Chain n-Alkanes by Mucorales IV" *European Journal of Applied Microbiology and Biotechnology*, vol. 5, pp. 189-195.
Ainsworth, G. C., and Bisby, G. R. 1954. "Systematic Arrangement of the Genera of Myxothallophyta and Eumycetes". In *A Dictionary of the Fungi*, Fourth Edition; Commonwealth Mycological Institute, Kew, Surrey, pp. 386-388.
Hortmann, L, and Rehm, H. J., 1984. "Inhibitory Effect of Undecanoic Acid on the Biosynthesis of Long-Chain Fatty Acids in *Mortierella isabellina*". *Applied Microbiology & Biotechnology*, vol. 20, pp. 139-145.
Hoffmann, B., and Rohm, H. J. 1976a. "Degradation of Long-Chain n-Alkanes by Mucorales. I." *European Journal of Applied Microbiology*, vol. 3, pp. 19-30.
Hoffmann, B., and Rehm, H. J. 1976b. "Degradation of Long-Chain n-Alkanes by Mucorales. II." *European Journal of Applied Microbiology*, vol. 3, pp. 31-41.
List of Cultures 1987 Centraalbureau Voor Schimmelcultures, Netherlands.
Institute for Fermentation Osaka-List of Cultures 1988 Eighth Edition, vol. 1, Japan.
Institute for Fermentation Osaka-List of Cultures 1978 Sixth Edition, Japan.

*Primary Examiner*—Richard A. Schwartz
*Assistant Examiner*—Mary E. Mosher
*Attorney, Agent, or Firm*—Burns, Doane, Swecker & Mathis

[57] ABSTRACT

A process for the production of a highly unsaturated fatty acid having an odd number of carbon atoms by culturing a microorganism belong to the genus Mortierella and capable of producing the fatty acid; and a process for the production a highly unsaturated fatty acid having an odd number of carbon atoms, typically represented by 8,11,14-nonadecatrienoic acid, by culturing a microorganism capable of producing arachidonic acid.

4 Claims, No Drawings

PROCESS FOR PRODUCTION OF HIGHLY UNSATURATED FATTY ACID HAVING ODD NUMBER OF CARBON ATOMS

BACKGROUND OF THE INVENTION

1. Field of the Invention

The present invention relates to a process for the production of fatty acids which have at least three double bonds (highly unsaturated) and have an odd number, preferably 17 to 21, of carbon atoms.

2. Description of the Related Art

It is known that fatty acid with an odd number of carbon atoms, such as pentadecanoic acid and heptadecanoic acid, are components of an animal oil, but the content thereof in the oil is very low, and therefore, an isolation and purification thereof is not cost effective. A process for the production of pentadecanoic acid has been proposed wherein n-alkane is used as a substrate for an accumulation of pentadecanoic acid among fatty acids in or outside of an alkane-assimilating microorganism, but a process for the production of a highly unsaturated fatty acid having an odd number of carbon atoms is not known. Nevertheless, an efficient process for the production of a highly unsaturated fatty acid having an odd number of carbon atoms is urgently required.

SUMMARY OF THE INVENTION

Accordingly, the present invention provides a process whereby highly unsaturated fatty acids having an odd number of carbon atoms can be efficiently produced by using an inexpensive culture medium.

More specifically, the present invention provides a process for the production of a highly unsaturated fatty acid having an odd number of carbon atoms, comprising the steps of:

culturing a microorganism belonging to the genus Mortierella and capable of producing a highly unsaturated fatty acid having an odd number of carbon atoms, to produce the highly unsaturated fatty acid having an odd number of carbon atoms or a lipid containing the highly unsaturated fatty acid having an odd number of carbon atoms; and recovering the highly unsaturated fatty acid having an odd number of carbon atoms.

Moreover, the present invention provides a process for the production of a lipid containing a highly unsaturated fatty acid having an odd number of carbon atoms, comprising the steps of:

culturing a microorganism belonging to the genus Mortierella and capable of producing a highly unsaturated fatty acid having an odd number of carbon atoms, to produce a lipid containing the highly unsaturated fatty acid having an odd number of carbon atoms; and recovering the lipid containing highly unsaturated fatty acid having an odd number of carbon atoms.

The present invention also provides a process for the production of a highly unsaturated fatty acid having an odd number of carbon atoms, comprising the steps of:

culturing a microorganism capable of producing arachidonic acid in a medium containing an additive selected from the group consisting of a hydrocarbon having an odd number of carbon atoms, a fatty acid having an odd number of carbon atoms, an ester of a fatty acid having an odd number of carbon atoms, a salt of a fatty acid having an odd number of carbon atoms, and a lipid containing the fatty acid, to produce a highly unsaturated fatty acid having an odd number of carbon atoms or a lipid containing a highly unsaturated fatty acid having an odd number of carbon atoms; or adding the additive to a culture medium in which the microorganism has been grown, and then further culturing the microorganism to produce a highly unsaturated fatty acid having an odd number of carbon atoms or a lipid containing a highly unsaturated fatty acid having an odd number of carbon atoms; and recovering the highly unsaturated fatty acid having an odd number of carbon atoms.

The present invention moreover provides a process for the production of a lipid containing a highly unsaturated fatty acid having an odd number of carbon atoms, comprising the steps of:

culturing a microorganism capable of producing arachidonic acid in a medium containing an additive selected from the group consisting of a hydrocarbon having an odd number of carbon atoms, a fatty acid having an odd number of carbon atoms, an ester of a fatty acid having an odd number of carbon atoms, a salt of a fatty acid having an odd number of carbon atoms, and a lipid containing the fatty acid, to produce a lipid containing a highly unsaturated fatty acid having an odd number of carbon atoms; or adding the additive to a culture medium in which the microorganism has been grown, and then further culturing the microorganism to produce a lipid containing a highly unsaturated fatty acid having an odd number of carbon atoms; and recovering the lipid containing highly unsaturated fatty acid having an odd number of carbon atoms.

The present invention also provides a process for the production of 8,11,14-nonadecatrienoic acid, comprising the steps of:

culturing a microorganism capable of producing arachidonic acid in a culture medium containing an additive selected from the group consisting of sesame oil, peanut oil, and a mixture thereof, to produce 8,11,14-nonadecatrienoic acid or a lipid containing 8,11,14-nonadecatrienoic acid; or adding the additive to a culture medium in which the microorganism has been grown, and then further culturing the microorganism to produce 8,11,14-nonadecatrienoic acid or a lipid containing 8,11,14-nonadecatrienoic acid; and recovering the 8,11,14-nonadecatrienoic acid.

The present invention also provides a process for the production of a lipid containing 8,11,14-nonadecatrienoic acid, comprising the steps of:

culturing a microorganism capable of producing arachidonic acid in a culture medium containing an additive selected from the group consisting of sesame oil, peanut oil, and a mixture thereof, to produce a lipid containing 8,11,14-nonadecatrienoic acid; or adding the additive to a culture medium in which the microorganism has been grown, and then further culturing the microorganism to produce a lipid containing 8,11,14-nonadecatrienoic acid; and recovering the lipid containing 8,11,14-nonadecatrienoic acid.

The present invention further provides a process for the production of 8,11,14-nonadecatrienoic acid comprising the steps of:

culturing a microorganism capable of producing arachidonic acid in a culture medium containing an additive selected from the group consisting of an extract from sesame oil with a solvent which is substantially immiscible with the sesame oil and an extract from sesame seeds with a solvent which is substantially immiscible with the sesame oil to produce 8,11,14- nonadecatrienoic acid or a lipid containing 8,11,14-nonadecatrienoic acid; or adding the additive to a culture medium in which the microorganism has been grown, and then further culturing the microorganism to produce 8,11,14-nonadecatrienoic acid or a lipid containing 8,11,14-nonadecatrienoic acid; and recovering the 8,11,14-nonadecatrienoic acid.

The present invention also provides a process for the production of a lipid containing 8,11,14-nonadecatrienoic acid, comprising the steps of:

culturing a microorganism capable of producing arachidonic acid in a culture medium containing an additive selected from the group consisting of an extract extracted from sesame oil with a solvent which is immiscible with the sesame oil and an extract from sesame seeds to produce a lipid containing 8,11,14-nonadecatrienoic acid; or adding the additive to a culture medium in which the microorganism has been grown, and then further culturing the microorganism to produce a lipid containing 8,11,14-nonadecatrienoic acid; and recovering the lipid containing 8,11,14-nonadecatrienoic acid.

The present invention provides another process for the production of 8,11,14-nonadecatrienoic acid, comprising the steps of:

culturing a microorganism capable of producing arachidonic acid in a culture medium containing an additive selected from the group consisting of sesamin, sesaminol, episesamin, episesaminol, and a mixture thereof, to produce 8,11,14-nonadecatrienoic acid or a lipid containing 8,11,14-nonadecatrienoic acid; or adding the additive to a culture medium in which the microorganism has been grown, and then further culturing the microorganism to produce 8,11,14-nonadecatrienoic acid or a lipid containing 8,11,14-nonadecatrienoic acid; and recovering the 8,11,14-nonadecatrienoic acid.

The present invention still further provides a process for the production of a lipid containing 8,11,14-nonadecatrienoic acid, comprising the steps of:

culturing a microorganism capable of producing arachidonic acid in a culture medium containing an additive selected from the group consisting of sesamin, sesaminol, episesamin, episesaminol, and a mixture thereof, to produce a lipid containing 8,11,14-nonadecatrienoic acid; or adding the additive to a culture medium in which the microorganism has been grown, and then culturing the microorganism to produce a lipid containing 8,11,14-nonadecatrienoic acid; and recovering the lipid containing 8,11,14-nonadecatrienoic acid.

DESCRIPTION OF THE PREFERRED EMBODIMENT

Highly unsaturated fatty acids having an odd number of carbon atoms produced according to the present invention are, for example, fatty acids having at least three double bonds in the carbon chain thereof and having 17 to 21 carbon atoms, such as 6,9,12-heptadecatrienoic acid, 8,11,14-nonadecatrienoic acid, 5,8,11,14-nonadecatetraenoic acid, and the like.

According to an embodiment of the present invention, any microorganism belonging to the genus Mortierella and capable of producing a highly unsaturated fatty acid can be used as a producer strain. According to another embodiment of the present invention, any microorganism capable of producing arachidonic acid can be used as the producer microorganisms.

These microorganisms include those belonging to the genera Mortierella, Conidiobolus, Pythium, Phytophthora, Penicillium, Cladosporium, Mucor, Fusarium, Aspergillus, Rhodotorula, and Entomophthora. Microorganisms belonging to the genus Mortierella include, for example, *Mortierella elongata* IFO 8570, *Mortierella exigua* IFO 8571, *Mortierella hygrophila* IFO 5941, *Mortierella alpina* IFO 8568 and *Mortierella parvisopora* IFO 8574. Other strains which can be used in the present invention include *Conidiobolus heterosporus* CBS 138.57, *Pythium irregulare* CBS 494.86, *Phytophthora infestans* IFO 4872, *Conidiobolus thromoboides* CBS 183.60, *Penicillium cyaneum* IFO 5337, *Cladosporium herbarum* IFO 30314, *Mucor ambiguus* IFO 6742, *Aspergillus candidus* IFO 8816, *Rhodotorula glutinis* IFO 0695, *Fusarium oxysporum* IFO 5942, *Caldosporium sphaerospermum* IFO 6377, and *Entomophthora ignobilis* CBS 181.60.

The above-mentioned strains having an IFO number are stored in the Osaka Institute for Fermentation; 17-85, Joso-honmachi 2-chome, Yodogawa-ku, Osaka 532, Japan, and are available to the public without limitation. The above-mentioned strains having a CBS number are stored in the Central Bureau Voor Schimmelcultures, Boorn, Netherlands, and are available to the public without limitation.

Moreover, a strain *Mortierella elongata* SAM 0219, can be used. This strain was newly isolated from soil and identified by the present inventors, and was deposited with the Fermentation Research Institute, Agency of Industrial Science and Technology (FRI), Higashi 1-1-3, Tsukuba-shi, Ibaraki-ken, Japan as FERM P-8703 on Mar. 19, 1986, and transferred to International Deposition under the Budapest Treaty as FERM BP-1239 on Dec. 22, 1986.

Spores, mycelia, or a preculture are used as an inoculum for culturing the present strains. The medium used may be a liquid or solid medium. A liquid medium contains as a carbon source, for example, glucose, fructose, xylose, saccharose, maltose, soluble starch, molasses, glycerol, or mannitol. Nitrogen sources include organic substances such as peptone, yeast extract, meat extract, casamino acid, corn steep liquor, urea and inorganic substances such as sodium nitrate, ammonium nitrate, ammonium sulfate, and the like. If necessary, inorganic salts such as phosphate salts, magnesium sulfate, ferrous sulfate and cupric sulfate, and vitamins may be included in a medium. The concentration of these components is selected such that the components do not adversely affect the growth of the microorganism used. Practically, the concentration of the carbon source is 0.1 to 30% by weight, preferably 1 to 10% by weight, relative to the total weight of the medium. The concentration of the nitrogen source is 0.01 to 5% by weight, preferably 0.1 to 2% by weight, relative to the total weight of the medium.

The culturing temperature is from 5° C. to 40° C., and the pH value of the medium is 4 to 10, preferably 6 to 9.

Culturing is preferably carried out with aeration and/or agitation, while shaking in a liquid medium, or while standing, and is usually carried out for 2 to 10 days.

When culturing is carried out in a solid medium, the solid medium is composed of wheat bran, chaff or rice bran supplemented with water in an amount of 50 to 100% by weight relative to the wheat bran, chaff or rice bran. If necessary, the medium is supplemented with a small amount of nitrogen source, inorganic salts, and or minor nutrients. Culturing is carried out at a temperature of 5° C. to 40° C., preferably 20° C. to 30° C., for 3 to 14 days.

According to an embodiment of the present invention, a microorganism belonging to the genus Mortierella and capable of producing a highly unsaturated fatty acid having an odd number of carbon atoms is cultured in a medium to produce the desired fatty acid.

According to another embodiment of the present invention, a microorganism capable of producing arachidonic acid is cultured in a medium containing a substrate having an odd number of carbon atoms. In this case, the substrates having an odd number of carbon atoms include hydrocarbons having an odd number of carbon atoms, such as undecane, tridecane, pentadecane, heptadecane, nonadecane and the like; fatty acids having an odd number of carbon atoms, such as undecanoic acid, tridecanoic acid, pentadecanoic acid, heptadecanoic acid, nonadecanoic acid, and the like; salts of fatty acids having an odd number of carbon atoms, such as sodium salt, potassium salt or ammonium salt of the above-mentioned fatty acids; esters of fatty acids, such as methyl ester, ethyl ester, propyl ester or coenzyme A ester of the above-mentioned fatty acids; and lipids containing the above-mentioned fatty acids. The above-mentioned substrate or combination thereof is added in an amount of 0.001 to 10% by weight and preferably 0.5 to 10% by weight relative to a medium.

The above-mentioned additive can be added to a culture medium before inoculation, or immediately after inoculation and before the onset of culturing. Alternatively, the additive can be added to a medium during culturing, or both before the onset of culturing and during culturing. When such an additive is used during culturing, it is added at one time, stepwise, or continuously.

According to another embodiment of the present invention, a microorganism capable of producing arachidonic acid is cultured in a medium containing an additive, to produce 8,11,14-nonadecatrienoic acid. The additives include sesame oil, peanut oil, and a mixture of these oils. These oils can be in a crude form or a purified form.

Moreover, the additive can be an extract from sesame oil. To obtain the extract, sesame oil is extracted with an organic solvent which is substantially immiscible with the sesame oil and can extract and dissolve effective ingredients. The organic solvents are, for example, acetone, methyl ethyl ketone, diethyl ketone, methanol, ethanol, and the like. To extract the effective ingredients, for example, sesame oil and the solvent are homogeneously mixed, and the mixture is allowed to stand at a low temperature. Phases are separated by a conventional procedure such as centrifugation to obtain an organic phase, which is then evaporated to obtain an extract. Alternatively, an extract useful for the present invention can be obtained from sesame seeds. In this case, sesame seeds, if necessary after grinding, are extracted with any solvent able to extract the sesame oil, for example, an organic solvent described above. After separating the solvent from the residue, the solvent is evaporated to obtain an extract. An extract obtained from sesame oil or sesame seeds contains lignans such as sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxyphenoxy)-3,7-dioxabicyclo [3.3.0] octane. Therefore, in accordance with the present invention, the above-mentioned compound alone, or any combination of at least two of the above-mentioned compounds, can be used as the additive. All of the above-mentioned compounds are known and are commercially available. Alternatively, there compounds can be isolated from the above-mentioned extract from sesame oil or sesame seeds. To this end, the extract can be separated by a conventional procedure, such as column chromatography, high performance liquid chromatography, distillation, crystallization, or a combination thereof.

The amount of the additive to be added to a culture medium is approximately as follows. Sesame oil, peanut oil, or a total amount of a mixture thereof, at 0.001 to 10% by weight, preferably 0.5 to 10% by weight relative to the amount of the medium. The extract from sesame oil or sesame seeds is used in an amount of $3 \times 10^{-3}$ to $3 \times 10^{-1}\%$ by weight relative to the amount of the medium. The above-mentioned lignan compounds are used in an amount of $1 \times 10^{-3}$ to $1 \times 10^{-1}\%$ by weight relative to the amount of the medium. Where a mixture of two or more lignans is used, this amount is intended to be a total amount of the mixture.

The above-mentioned additive can be added to a culture medium before inoculation, or immediately after inoculation and before the onset of culturing. Alternatively, the additive can be added to a medium during culturing, or both before the onset of culturing and during culturing. When such an additive is used during culturing, it is added at one time, stepwise, or continuously.

During the culturing, a lipid containing a large amount of highly unsaturated fatty acid having an odd number of carbon atoms is intracellularly accumulated. Where culturing is carried out in a liquid medium, highly unsaturated fatty acid having an odd number of carbon atoms is recovered, for example, as follows. After the culturing cells are collected from the culture broth by a conventional means such as filtration or centrifugation, the cells are washed with water, and preferably, the washed cells are dried.

Drying is carried out by, for example, lyopilization or air drying. The dried product is treated with an organic solvent or a mixture thereof, preferably under a nitrogen stream, to extract a lipid containing a highly unsaturated fatty acid having an odd number of carbon atoms. The organic solvent or mixture thereof is, for example, ethers such as ethyl ether, hydrocarbons such as hexane, alcohols such as methanol or ethanol, halo-hydrocarbons such as chloroform or dichloromethane, petroleum ether, as well as a mixture of chloroform, methanol and water, or a combination of methanol and petroleum ether alternately used. By distilling off the solvent, a lipid containing a highly unsaturated fatty acid having an odd number of carbon atoms is obtained.

Alternatively, wet cells or the culture broth can be subjected to direct extraction. In such a case, a water-miscible solvent such as methanol or ethanol, or a water miscible solvent mixture comprising the water-miscible solvent and water or other organic solvent is used. The extraction procedure is the same as described for dried cells.

The lipid thus obtained contains a highly unsaturated fatty acid having an odd number of carbon atoms in the form of a lipid compound such as fat. Although a highly unsaturated fatty acid having an odd number of carbon atoms can be isolated in the form of a free highly unsaturated fatty acid having an odd number of carbon atoms, it is preferably isolated in the form of an ester with a lower alcohol, for example, as methyl ester, such as methyl 9-heptadecenoate, methyl 9,12-heptadecadienoate, methyl 8,11,14,-nonadecatrienoate, methyl 5,8,11,14-nonadecatetraenoate, and the like. By converting highly unsaturated fatty acid having an odd number of carbon atoms to such an ester, it is easily separated from other lipid components, and from other undesirable fatty acids formed during culturing, such as palmitic acid, oleic acid, linoleic acid and the like, which are also esterified at the same time as a highly unsaturated fatty acid having an odd number of carbon atoms is esterified. To obtain methyl ester of a highly unsaturated fatty acid having an odd number of carbon atoms, for example, the lipid prepared as described above is treated with a 5 to 10% hydrochloric acid solution in absolute methanol or a 10 to 50% $BF_3$ solution in methanol for 1 to 24 hours at a room temperature.

The mixture thus obtained is extracted with an organic solvent such as hexane, ethyl ether or ethyl acetate, to recover methyl ester of highly unsaturated fatty acid having an odd number of carbon atoms. Next, the extract is dried over anhydrous sodium sulfate, and the solvent is distilled off under a reduced pressure to obtain a residue mainly comprising a fatty acid mixture The mixture contains, in addition to methyl ester of a highly unsaturated fatty acid having a odd number of carbon atom, fatty acids having an even number of carbon atoms such as methyl plamitate, methyl stearate, methyl oleate and the like. From the mixture, methyl ester of a highly unsaturated fatty acid having a odd number of carbon atoms is isolated by column chromatography, low temperature crystallization, a urea adducting method, or a combination thereof.

The isolated methyl ester of a highly unsaturated fatty acid having an odd number of carbon atoms is then hydrolyzed with an alkali and extracted with an organic solvent such as ethyl ether, ethyl acetate, or the like to obtain a highly unsaturated fatty acid having an odd number of carbon atoms in a free form.

Alternatively, a highly unsaturated fatty acid having an odd number of carbon atoms can be obtained, without conversion to methyl ester, by alkalolysis with, for example, 5% sodium hydroxide at a room temperature for 2 to 3 hours, followed by extraction of the fatty acids from the alkaloysis product and isolation of a highly unsaturated fatty acid having an odd number of carbon atoms.

EXAMPLES

The present invention will now be further illustrated by, but is by no means limited to, the following examples.

EXAMPLE 1

Two ml of a medium containing 2.0% glucose and 1% yeast extract (pH 6.0) was put into Erlenmeyer flasks, and the whole was autoclaved at 120° C. for 20 minutes. *Mortierella alpina* CBS 219.35, and *Mortierella hygrophila* IFO 5941 were separately inoculated to the above-mentioned medium, and cultured on a reciprocating shaker at 110 rpm, for seven days at 28° C. After the culturing, each culture broth was filtered to obtain cultured cells, which were then washed with water and dried in a centrifugal evaporator at 60° C. for two hours. To the dried cells were added 2 ml of methylene chloride and 2 ml of 10% hydrochloric acid in absolute methanol, and the whole was incubated at 50° C. for three hours to esterify produced fatty acids. To the mixture were added 4 ml of n-hexane and 1 ml of water to extract the fatty acids methyl esters. The extraction was carried out twice, and the extractant were combined and evaporated in a centrifugal evaporator at 40° C. for one hour to eliminate the solvent. The fatty acid methyl esters thus obtained were analyzed by gas chromatography. As a result, *Mortierella alpina* CBS 219.35 and *Mortierella hydrophila* IFO 5941 produced 5,8,11,14-nonadecatetraenoic acid in an amount of 3 mg/l culture broth and 1 mg/l culture broth, respectively.

5,8,11,14-nonadecatetraeonic acid was isolated by separating the fatty acid methyl esters obtained as described above using high performance liquid chromatography on a reverse column ($5C_{18}$) with acetonitrile/water (85:15) as the eluate. The 5,8,11,14-nonadecatetraenoic acid thus obtained was confirmed by mass spectrometry and NMR spectrometry, and the following result was obtained.

Mass spectrometry
Molecular ion peak m/z 304.
$^1$H-NMR ($CD_2Cl_2$) 0.90 ppm (t, 3H, $CH_3$), 1.34 ppm (m, 4H, $CH_2$), 1.68 ppm (m, 2H, $CH_2$), 2.09 ppm (m, 4H, $CH_2$), 2.30 ppm (t, 2H, $CH_2$), 2.83 ppm (m, 6H, $CH_2$), 3.63 ppm (s, 3H, $CH_3$), 5.38 ppm (m, 8H, C=C).

EXAMPLE 2

Two ml of a medium containing 1% pentadecane or 0.5% heptadecane or 0.5% nonadecane, and 2% glucose and 1% yeast extract (pH 6.0), or 2 ml of a medium containing 2% pentadecane and 1% yeast extract (pH 6.0) was put into a 10 ml Erlenmeyer flask, and the whole was autoclave at 120° C. for 20 minutes. 100 μl of a spore suspension of *Morterella alpina* CBS 219.35 was inoculated to each medium, and culturing was carried out on a reciprocating shaker at 110 rpm, at 28° C. for 6 days. After the culturing, each culture broth was filtrated to recover cultured cells, which were then thoroughly washed with water. The washed cells were dried in a centrifugal evaporation, and the dried cells were subjected to hydrolysis, methyl-esterification, and extraction as described in Example 1, and fatty acid methyl esters thus obtained were analyzed by gas chromatography. The results are shown in Table 1.

TABLE 1

| | Production of fatty acid per medium where n-alkane is used as substrate (mg/l) | | | |
|---|---|---|---|---|
| | Substrate | | | |
| Fatty acid produced* | Pentodecane (C15) | Heptadecane (C17) | Nonadecane (C19) | Carbon source C15 only |
| 15:0 | 649.0 | 59.0 | 21.0 | 849.0 |
| 16:0 | 319.0 | 499.0 | 423.0 | 12.0 |
| 16:1 | — | 12.0 | 10.0 | — |
| 17:0 | 325.0 | 282.0 | 74.0 | 306.0 |
| 17:1 | 217.0 | 138.0 | 31.0 | 371.0 |
| 17.2 | 129.0 | 101.0 | 13.0 | 126.0 |
| 17:3 | 22.0 | 16.0 | 5.0 | 71.0 |
| 18:0 | 171.0 | 193.0 | 282.0 | 7.0 |
| 18:1 | 312.0 | 642.0 | 685.0 | 43.0 |
| 18:2 | 191.0 | 179.0 | 170.0 | 42.0 |
| 18:3γ | 139.0 | 128.0 | 132.0 | 30.0 |
| 19:0 | 9.0 | 15.0 | 60.0 | 20.0 |
| 19:1 | 49.0 | trace | trace | 81.0 |
| 19:2 | 9.0 | trace | trace | 26.0 |
| 19:3 | 26.0 | 9.0 | 8.0 | 59.0 |
| 19:4 | 129.0 | 24.0 | 10.0 | 247.0 |
| 20:1 | 15.0 | 28.0 | 26.0 | — |
| 20:2 | — | — | — | — |
| 20:3 | 138.0 | 110.0 | 117.0 | 8.0 |
| 20:4 | 976.0 | 554.0 | 531.0 | 83.0 |

TABLE 1-continued

| Fatty acid produced* | Production of fatty acid per medium where n-alkane is used as substrate (mg/l) | | | |
|---|---|---|---|---|
| | Substrate | | | Carbon source C15 only |
| | Pentodecane (C15) | Heptadecane (C17) | Nonadecane (C19) | |
| 21:0 | 20.0 | 11.0 | 32.0 | 22.0 |
| 23:0 | 20.7 | trace | 13.0 | 25.0 |

*15:1 = pentadecanoic acid; 16:0 = palmitic acid; 17:0 = heptadecanoic acid; 17:1 = 9-peptadecanoic acid; 17:2 = 9,12-heptadecadienic acid; 17:3 = 6,9,12-heptadecatrienoic acid; 18:0 = stearic acid; 18:1 = oleic acid; 18:2 = linoleic acid 18:3γ = linolenic acid; 19:0 = nonadecanoic acid; 19:3 = 8,11,14-nonadecatrienoic acid; 19:4 = 5,8,11,14-nonadecatetraenoic acid; 20:3 = bishomo-γ-linolenic acid; 20:4 = arachidonic acid; 21:0 = heneicosanoic acid; 23:0 = tricosamoic acid As seen from Table 1, highly unsaturated fatty acids having an odd number of carbon atoms are produced in a large amount by an addition of n-alkane having an odd number of carbon atoms, i.e., pentadecane (C15), heptadecane (C17) or nonadecane (C19). Moreover, where n-alkane having an odd number of carbon atoms, i.e., pentadecane, is used as a role carbon source, a further increased production of highly unsaturated fatty acids having an odd number of carbon atoms was observed.

EXAMPLE 3

Two ml of a medium containing 2% glucose and 1% yeast extract as well as an additive selected from the group consisting of 1% pentadecanoic acid, 1% heptadecanoic acid, 1% methyl pentadecanoate, 1% methyl nonadecanoate, 1% tripentadecanoin and 1% triheptadecanoin was put into a 10 ml Erlenmeyer flask, and the whole was autoclaved at 120° C. for 20 minutes. 100 μl of a spore suspension of Mortierella alpina CBS 219.35 was inoculated to each medium, and culturing was carried out on a reciprocating shaker at 110 rpm and 28° C. for 6 days. After culturing, the filtration of the cultured broth, washing cells with water, drying of cells, hydrolysis of the lipid, methyl-esterification of the fatty acids, and extraction of the methyl esters were carried out by the same procedures as described in Example 1. The fatty acid methyl esters thus obtained were analyzed by gas chromatography, and the results are shown in Table 2.

TABLE 2

| Substrate | Amount of 5,8,11,14-nonadecatetraenoic acid produced per culture broth (mg/l) |
|---|---|
| Pentadecanoic acid | 74.3 |
| Heptadecanoic acid | 16.7 |
| Methyl pentadecanoate | 113.0 |
| Methyl nonadecanoate | 9.2 |
| Tripentadecanoin | 102.4 |
| Triheptadecanoin | 7.7 |

As seen from Table 2, it is confirmed that when a fatty acid having an odd number of carbon atoms, an ester of a fatty acid having an odd number of carbon atoms, and a lipid containing a fatty acid having an odd number of carbon atoms are used as precursors, the production of 5,8,11,14-nonadecatetraenoic acid, a representative fatty acid of the present invention, was increased.

EXAMPLE 4

Two ml of a medium containing 2% glucose, 1% yeast extract and 1% methyl pentadecanoate (pH 6.0) was put into a 10 ml Erlenmeyer flask, and the whole was autoclaved at 120° C. for 20 minutes. Mortierella hygrophila IFO 5941 or Mortierella alpina CBS 219.35 was inoculated to the medium, and culturing was carried out on a reciprocating shaker at 110 rpm and 28° C. for 6 days. Filtration of the cultured broth, washing the cells with water, drying the cells, hydrolysis of the fatty acids, methyl-esterification of the fatty acids, and extraction of the methyl esters are carried out by the same procedures as described in Example 1 to obtain a mixture of the fatty acid methyl esters. The mixture was analyzed by gas chromatography, and the results are shown in Table 3.

TABLE 3

| Producer strain | Fatty acid produced (mg/l culture broth) | | | |
|---|---|---|---|---|
| | 18:3γ | 20:3 | 20:4 | 19:4 |
| M. hygrophila IFO 5941 | 51.6 | 20.3 | 68.0 | 16.3 |
| M. alpina CBS 219.35 | 63.1 | 27.5 | 124.0 | 18.5 |

18:3γ = γ-linolenic acid
20:3 = bishomo-γ-linolenic acid
20:4 = arachidonic acid
19:4 = 5,8,11,14,-nonadecatetraenoic acid As seen from Table 3, when a microorganism capable of producing arachidonic acid is cultured in a medium containing a substrate having an odd number of carbon atoms, highly unsaturated fatty acids having an odd number of carbon atoms, such as a 5,8,11,14-nonadecatetraenoic acid, are produced.

EXAMPLE 5

Two ml of a medium containing 2% glucose, 1% yeast extract, 1% methyl pentadecanoate and 1% sesame oil (pH 6.0); or 2 ml of a medium containing 2% glucose, 1% yeast extract, 1% methyl pentadecanoate and 1% peanut oil (pH 6.0); and a medium containing 2% glucose, 1% yeast extract, 1% methyl pentadecanoate and 1% olive oil (pH 6.0) was put into a 10 ml Erlenmeyer flask, and the whole was autoclaved at 120° C. for 20 minutes. 100 μl of a spore suspension of Mortierella alpina CBS 219.53 was inoculated to each medium, and culturing was carried out on a reciprocating shaker at 110 rpm and 28° C. for 6 days. Filtration of the cultured broth, washing the cells with water, drying the cells, hydrolysis of the fatty acids, methyl-esterification of the fatty acids, and extraction of the methyl esters are carried out by the same procedures as described in Example 1 to obtain a mixture of the fatty acid methyl esters. The mixture was analyzed by gas chromatography, and the results are shown in Table 4.

TABLE 4

| Fatty acid produced | Amount of fatty acid produced per culture broth (mg/l) | | |
|---|---|---|---|
| | Additive | | |
| | Sesame oil | Olive oil | Peanut oil |
| 8,11,14-Nonadecatrienoic acid (19:3) | 94.6 | 57.3 | 73.3 |
| 5,8,11,14-Nonadecatetraenoic acid (19:4) | 126.0 | 110.0 | 106.0 |
| Bishomo-γ-linolenic acid (20:3) | 257.0 | 142.0 | 213.0 |
| Arachidonic acid (20:4) | 859.0 | 975.0 | 924.0 |

An addition of sesame oil or peanut oil, suppresses the production of 5,8,11,14-nonadecatetraenoic acid and enhances the production of 8,11,14-nonadecatrienoic acid. An addition of olive oil does not enhance the production of 8,11,14-nonadecatrienoic acid.

EXAMPLE 6

Two ml of a medium containing 2% glucose, 1% yeast extract and 1% methyl pentadecanoate (pH 6.0) was put into a 10 ml Erlenmeyer flask, and the whole was autoclaved at 120° C. for 20 minutes.

*Conidiobolus heterosporus* CBS 138.57, *Pthium irregulare* CBS 494.86, *Phytophthora infestans* IFO 4872, *Entomophthora ignobilis* CBS 181.60, *Penicillium cyaneum* IFO 5337, *Cladosporium herbarum* IFO 30314, *Mucor ambiguus* IFO 6742, *Aspergillus candidus* IFO 8816, *Rhodotorula glutinis* IFO 0695, or *Fusarium oxysporum* IFO 5942 was inoculated to the medium, and culturing was carried out on a reciprocating shaker at 110 rpm, for 7 days at 28° C. Filtration of the cultured broth, washing the cells with water, drying the cells, hydrolysis of the fatty acids, methyl-esterification of the fatty acids, and extraction of the methyl esters are carried out by the same procedures as described in Example 1 to obtain a mixture of the fatty acid methyl esters. The mixture was analyzed by gas chromatography, and the results are shown in Table 5.

TABLE 5

| Amount of 5,8,11,14-nonadecatetraenoic acid (19:4) produced per culture broth (mg/l) | |
|---|---|
|  | Amount of 19:4 produced |
| *Conidiobolus heterosporus* CBS 138.57 | 98.2 |
| *Pythium irregulare* CBS 494.86 | 40.1 |
| *Phytophthora infestans* IFO 4872 | 17.7 |
| *Entomophthora ignobilis* CBS 181.60 | 22.6 |
| *Penicillium cyaneum* IFO 5337 | 14.2 |
| *Cladosporium herbarum* IFO 30314 | 25.0 |
| *Mucor ambiguus* IFO 6742 | 8.3 |
| *Aspergillus candidus* IFO 8816 | 6.2 |
| *Rhodotorula glutinis* IFO 0695 | 11.9 |
| *Fusarium oxysporus* IFO 5942 | 6.7 |

The production of highly unsaturated fatty acids having an odd number of carbon atoms was confirmed by culturing a microorganism capable of producing arachidonic acid in a medium containing a substrate having an odd number of carbon atoms.

EXAMPLE 7

Two ml of a medium containing 2% glucose, 1% yeast extract and 2% pentadecane (pH 6.0), or 2 ml of and a medium containing 2% glucose, 1% yeast extract, 2% pentadecane and 0.01% sesamin (pH 6.0) was put into a 10 ml Erlenmeyer flask, and the whole was autoclaved at 120° C. for 20 minutes. 100 μl of a spore suspension of *Mortierella alpina* CBS 219.35 was inoculated to each medium, and culturing was carried out on a reciprocating shaker at 110 rpm, for 6 days at 28° C. Filtration of the cultured broth, washing the cells with water, drying the cells, hydrolysis of the fatty acids, methyl-esterification of the fatty acids, and extraction of the methyl esters are carried out by the same procedures as described in Example 1 to obtain a mixture of the fatty acid methyl esters. The mixture was analyzed by gas chromatography, and the results are shown in Table 6.

TABLE 6

| Amount of fatty acid produced per culture broth (mg/l) | | |
|---|---|---|
|  | Additive | |
| Fatty acid produced | Sesamin − | Sesamin + |
| 8,11,14-Nonadecatrienoic acid (19:3) | 34.0 | 129.0 |
| 5,8,11,14-Nonadecatetraenoic acid (19:4) | 110.0 | 59.2 |
| Bishomo-γ-linolenic acid (20:3) | 124.0 | 484.0 |
| Arachidonic acid (20:4) | 856.0 | 671.0 |

As seen from Table 6, by adding sesamin to a medium and culturing a producer microorganism or adding sesamin 30 to a cultured broth and further culturing a producer microorganism, the production of bishomo-γ-linolenic acid and the production of 8,11,14-nonadecatrienoic acid is increased.

We claim:

1. A process for the production of highly unsaturated fatty acid having an odd number of carbon atoms, comprising the steps of:
   culturing *Mortierella hygrophila* IFO 5941 to produce the highly unsaturated fatty acid having an odd number of carbon atoms or a lipid containing the highly unsaturated fatty acid having an odd number of carbon atoms; and
   recovering the highly unsaturated fatty acid having an odd number of carbon atoms.

2. A process for the production of a lipid containing a highly unsaturated fatty acid having an odd number of carbon atoms, comprising the steps of:
   culturing *Mortierella hygrophila* IFO 5941 to produce a lipid containing a highly unsaturated fatty acid having an odd number of carbon atoms; and
   recovering the lipid containing the highly unsaturated fatty acid having an odd number of carbon atoms.

3. A process for the production of a highly unsaturated fatty acid having an odd number of carbon atoms, comprising the steps of:
   culturing *Mortierella hygrophila* IFO 5941 in a medium containing an additive selected from the group consisting of pentadecane, heptadecane, nonadecane, pentadecanoic acid, heptadecanoic acid, nonadecanoic acid, methyl pentadecanoate, methyl heptadecanoate, methyl nonadecanoate, tripentadecanoin, triheptadecanoin and trinonadecanoin to produce a highly unsaturated fatty acid having an odd number of carbon atoms or a lipid containing a highly unsaturated fatty acid having an odd number of carbon atoms; or adding the additive to a culture medium in which the microorganism has been grown, and then further culturing the microorganism to produce a highly unsaturated fatty acid having an odd number of carbon atoms or a lipid containing a highly unsaturated fatty acid having an odd number of carbon atoms; and
   recovering the highly unsaturated fatty acid having an odd number of carbon atoms.

4. A process for the production of a lipid containing highly unsaturated fatty acid having an odd number of carbon atoms, comprising the steps of:
   culturing *Mortierella hygrophila* IFO 5941 in a medium containing an additive selected from the group consisting of pentadecane, heptadecane, nonadecane, pentadecanoic acid, heptadecanoic acid, nonadecanoic acid, methyl pentadecanoate, methyl heptadecanoate, methyl nonadecanoate, tripentadecanoin, triheptadecanoin and trinonadecanoin to produce a lipid containing a highly unsaturated fatty acid having an odd number of carbon atoms; or adding the additive to a culture medium in which the microorganism has been grown, and then further culturing the microorganism to produce a lipid containing a highly unsaturated fatty acid having an odd number of carbon atoms; and recovering the lipid containing the highly unsaturated fatty acid having an odd number of carbon atoms.

* * * * *